United States Patent [19]

Pearlman et al.

[11] Patent Number: 5,225,555
[45] Date of Patent: Jul. 6, 1993

[54] PROCESSES FOR PURIFICATION OF 2,4-DI(1-PYRROLIDINYL)-6-CHLOROPYRIMIDINE

[75] Inventors: Bruce A. Pearlman, Kalamazoo; Amphlett G. Padilla, Portage, both of Mich.

[73] Assignee: The Upjohn Company, Kalamazoo, Mich.

[21] Appl. No.: 932,193

[22] Filed: Aug. 19, 1992

Related U.S. Application Data

[63] Continuation of Ser. No. 813,869, Dec. 26, 1991, abandoned.

[51] Int. Cl.$^5$ ............................................. C07D 403/14
[52] U.S. Cl. ................................... 544/323; 544/295; 544/296; 544/122
[58] Field of Search ............... 544/323, 295, 296, 122

[56] References Cited

U.S. PATENT DOCUMENTS

| 4,025,515 | 5/1977 | Schneider | 260/256.4 |
| 4,082,535 | 4/1978 | Hoegerle | 260/256.4 |
| 4,996,318 | 2/1991 | Gall | 544/295 |

Primary Examiner—John M. Ford
Attorney, Agent, or Firm—Bruce Stein

[57] ABSTRACT

The present invention involves two processes for the purification of a mixture of 2,4-di(1-pyrrolidinyl)-6-chloropyrimidine (III)

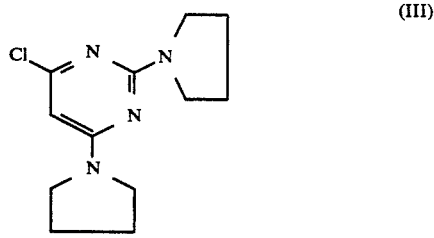

and 4,6-di(1-pyrrolidinyl)-2-chloropyrimidine (IV)

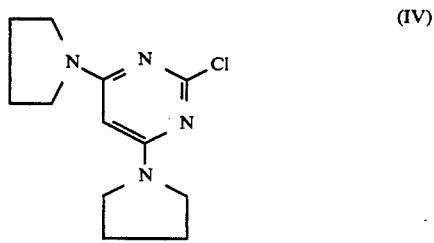

to where <1.0% of 4,6-di(1-pyrrolidinyl)-2-chloropyrimidine (IV) is present. In addition also disclosed is a process which not only purifies 2,4-di(1-pyrrolidinyl)-6-chloropyrimidine (III) but produces the commercially important 2,4-di(1-pyrrolidinyl)-6-(1-piperazinyl)pyrimidine (IX) directly.

29 Claims, No Drawings

PROCESSES FOR PURIFICATION OF 2,4-DI(1-PYRROLIDINYL)-6-CHLOROPYRIMIDINE

CROSS-REFERENCE TO RELATED APPLICATIONS

The present patent application is a continuation application of U.S. patent application Ser. No. 07/813,869, filed Dec. 26, 1991, now abandoned.

BACKGROUND OF THE INVENTION

1. Field of the Invention

The invention involves two processes to purify a known chemical compound, 2,4-di(1-pyrrolidinyl)-6-chloropyrimidine (III) and a modification whereby the 2,4-di(1-pyrrolidinyl)-6-chloropyrimidine (III) is transformed to the desired 2,4-di(1-pyrrolidinyl)-6-(1-piperazinyl)pyrimidine (IX) all in one process.

2. Description of the Related Art

U.S. Pat. No. 4,082,535 discloses that treatment of 2,4,6-trichloropyrimidine (I) with isopropyl amine results in a mixture of 2,4-di(isopropylamino)-6-chloropyrimidine and the 2-chloro isomer.

U.S. Pat. No. 4,025,515 discloses that treatment of 2,4,6-trichlorpyrimidine (I) with isopropyl amine under different (milder) conditions results in a mixture of 2-isopropylamino)-4,6-dichloropyrimidine and the corresponding 4-isopropylamino isomer.

U.S. Pat. No. 4,996,318 discloses that treatment of 2,4,6-trichloropyrimidine (I) with pyrrolidine (II) at 20°–25° for 4 hrs gives 2,4-di(1-pyrrolidinyl)-6-chloropyrimidine (III) in 74.0% yield. The yield of 4,6-di(1-pyrrolidinyl)-2-chloropyrimidine (IV) was not disclosed.

SUMMARY OF INVENTION

Disclosed is a process for purification of 2,4-di(1-pyrrolidinyl)-6-chloropyrimidine (III)

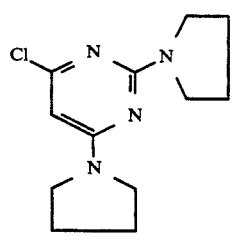

(III)

which comprises
(1) contacting a mixture 2,4-di(1-pyrrolidinyl)-6-chloropyrimidine (III) and 4,6-di(1-pyrrolidinyl)-2-chloropyrimidine (IV)

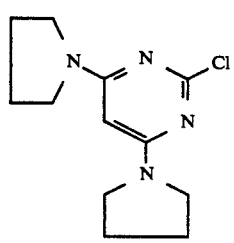

(IV)

with a weak purification reagent in the presence of a sufficient amount of an acid to make the pH less than 4 and
(2) separating the 2,4-di(1-pyrrolidinyl)-6-chloropyrimidine (III) by physical means from the pyrimidine byproducts (V) and (VI).

Further disclosed is a process for purification of 2,4-di($NR_8R_9$)-6-chloropyrimidine (X) where $R_8$ annd $R_9$ are the same or different and are
—H,
$C_1$–$C_6$ alkyl,
—$CH_2$—CH=$CH_2$,
—$CH_2$—$CH_2$—$CH_2$-$OCH_3$,
—$\phi$ optionally substituted with 1 thru 3 —Cl, —$CH_3$
and where two of $R_8$ and $R_9$ can be taken together with the attached nitrogen atom to form a heterocyclic ring selected from the group consisting of piperazine, pyridine, pyrimidine and morpholine, which comprises
(1) contacting a mixture 2,4-di($NR_8R_9$)-6-chloropyrimidine (X) and 4,6-di($NR_8R_9$)-2-chloropyrimidine (XI) where $R_{8=}$ and $R_9$ are as defined above, with a weak purification reagent in the presence of a sufficient amount of an acid to make the pH less than 4 and
(2) separating the 2,4-di($NR_8R_9$)-6-chloropyrimidine (III) by physical means.

Additionally disclosed is a process for purification of 2,4-di($NR_8R_9$)-6-chloropyrimidine (X) where $R_8$ annd $R_9$ are the same or different and are
—H,
$C_1$–$C_6$ alkyl,
—$CH_2$—CH=$CH_2$,
—$CH_2$—$CH_2$—$CH_2$—$OCH_3$,
—$\phi$ optionally substituted with 1 thru 3 —Cl, —$CH_3$
and where two of $R_8$ and $R_9$ can be taken together with the attached nitrogen atom to form a heterocyclic ring selected from the group consisting of pyrrolidinyl, piperazinyl, pyridinyl, pyrimidinyl and morpholinyl, which comprises
(1) contacting a mixture 2,4-di($NR_8R_9$)-6-chloropyrimidine (X) and 4,6-di($NR_8R_9$)-2-chloropyrimidine (XI) where $R_{8=}$ and $R_9$ are as defined above, with a weak purification reagent in the presence of a sufficient amount of an acid to make the pH less than 4 and
(2) separating the 2,4-di($NR_8R_9$)-6-chloropyrimidine (III) by physical means.

Also disclosed is a process for the preparation of 2,4-di(1-pyrrolidinyl)-6-(1-piperazinyl)pyrimidine (IX) which comprises
(1) contacting a mixture 2,4-di(1-pyrrolidinyl)-6-chloropyrimidine (III) and 4,6-di(1-pyrrolidinyl)-2-chloropyrimidine (IV) with a weak purification reagent in the presence of a sufficient amount of an acid to make the pH less than 4 and
(2) contacting the reaction mixture of step (1) with piperazine.

DETAILED DESCRIPTION OF THE INVENTION 2,4-Di(1-pyrrolidinyl)-6-(1-piperazinyl)pyrimidine (IX) is known, see U.S. Pat. No. 4,996,318 and International Publication No. WO87/01706, published Mar. 26, 1987 based on International Patent Application No. PCT/US86/01797, PREPARATION A-22. 2,4-Di(1-pyrrolidinyl)-6-(1-piperazinyl)pyrimidine (IX) is an important intermediate useful in the preparation of 16α- methyl-21-[4-[2,6-di(1-pyrrolidinyl)-4-pyrimidinyl]-1-piperazinyl]pregna-1,4,9(11)-triene-3,20-dione, see International Publication No. WO87/01706 (EXAMPLE 83) and U.S. Pat. No. 4,968,675.

An obvious way to produce 2,4-di(1-pyrrolidinyl)-6-(1-piperazinyl)pyrimidine is from the readily available and reasonably inexpensive 2,4,6-trichlorpyrimidine (I). Replacement of the 2- and 4- chlorine atoms with pyrrolidine and the 6-chlorine with piperazine gives 2,4-di(1-pyrrolidinyl)-6-(1-piperazinyl)pyrimidine (IX).

However, this apparently simple process is precluded because the three chlorine atoms have similar reactivity. Treatment of 2,4,6-trichloropyrimidine (I) with 4.33 equivalents of pyrrolidine (II) results in formation of a mixture of 2,4-di(1-pyrrolidinyl)-6-chloropyrimidine (III) and 4,6-di(1-pyrrolidinyl)-2-chloropyrimidine (IV) in a ratio of 88.0/12.0 to 94.3/5.7 depending on the solvent used.

Not only does the prior art teach that a mixture of aminopyridine isomers are invariably generated, but that these isomers have similar physical properties making the mixture very difficult to purify and separate by physical means. For example, fractional crystallization is ineffectual. Crystallization of a 93.8/6.2 mixture from acetone/water resulted in only a modest degree of purification to a 95.7/4.3 mixture. About the same degree of purification occurs on recrystallization from other solvents such as ethyl acetate (95.8/4.2), methanol (95.0/5.0) and acetonitrile (95.5/4.5). Thus silica gel chromatography was found to be necessary for separation of these isomers, see J. Med. Chem. 33, 1145 (1990) and U.S. Pat. No. 4,996,318.

In theory, purification can be achieved by selective chemical substitution of the 2-chlorine of the undesired isomer 4,6-di(1-pyrrolidinyl)-2-chloropyrimidine (IV) by some nucleophile. For this strategy to be workable, the nucleophile must be much more reactive toward the 2-chloro isomer, 4,6-di(1-pyrrolidinyl)-2-chloropyrimidine (IV) as compared to the 2,4-di(1-pyrrolidinyl)-6-chloropyrimidine isomer (III) since otherwise significant amounts of the desired 4-chloro isomer (III) would be destroyed concurrently.

The very fact that 2,4,6-trichloropyrimidine (I) reacts with pyrrolidine to form a mixture of 2,4-di(1-pyrrolidinyl)-6-chloropyrimidine (III) and 4,6-di(1-pyrrolidinyl)-2-chloropyrimidine (IV) isomers is evidence that the 2-chlorine of 4,6-di(1-pyrrolidinyl)-2-chloropyrimidine (IV) and the 6-chlorine of the corresponding 2,4-di(1-pyrrolidinyl)-6-chloropyrimidine isomer (III) should have comparable reactivity. In addition, information published in the literature suggests that 2-chloropyrimidines and 6-chloropyrimidines are about equally reactive. For example, 2-chloro-4,6-dimethylpyrimidine reacts 1.3 times more slowly than 6-chloro-2,4-dimethylpyrimidine toward isopentylamine at 70°, see J. Chem. Soc. C 1889 (1971). Further, 2-chloropyrimidine is only 3.1 times as reactive as 4-chloropyrimidine toward piperidine in isooctane at 60°, see J. Org. Chem. USSR, 8, 589 (1972). Thus, 2,4-di(1-pyrrolidinyl)-6-chloropyrimidine (III) and 4,6-di(1-pyrrolidinyl)-2-chloropyrimidine (IV) are expected to react with nucleophiles at approximately equal rates.

The processes of the present invention involve two different ways (PROCESSES A and B) to accomplish the same result. PROCESS A involves use of a weak purification reagent, PROCESS B, involves the use of a strong purification reagent. In PROCESS A, a mixture of 2,4-di(1-pyrrolidinyl)-6-chloropyrimidine (III) and 4,6-di(1-pyrrolidinyl)-2-chloropyrimidine (IV) upon contacting with a weak purification reagent and an acid produces a mixture of (III), (IV), 2,4-di(1-pyrrolidinyl)-6-pyrimidone (V) and 4,6-di(1-pyrrolidinyl)-2-pyrimidone (VI). From this mixture which has an improved ratio of (III)/(IV), (III) is obtained as explained below. In PROCESS B, the mixture of (III) and (IV) is contacted with a strong purification reagent and produces a mixture of (III), (IV), 6-substituted-2,4-di(1-pyrrolidinyl)pyrimidines (VII) and 2-substituted-4,6-di(1-pyrrolidinyl)pyrimidines (VIII). From this mixture which has an improved ratio of (III)/(IV), (III) is obtained as explained below. Alternatively, the mixture of (III), (IV), (VII) and (VIII) is contacted with piperazine to produce a mixture of (IX), isomer of (IX), (VII) and (VIII) from which (IX) is isolated.

PROCESS A, requires contacting a mixture of 2,4-di(1-pyrrolidinyl)-6-chloropyrimidine (III) and 4,6-di(1-pyrrolidinyl)-2-chloropyrimidine (IV) with weak purification reagent in the presence of an acid. A weak purification reagent is one which is not sufficiently strong to react with 4,6-di(1-pyrrolidinyl)-2-chloropyrimidine (IV) in the absence of an acid. Weak purification reagents include water, glycerol, ethylene glycol, propylene glycol and alcohols of the formula $R_a(-O-CH_2-CH_2)_{n_1}-OH$ where $n_1$ is 0 thru 20 and where $R_a$ is $C_1$-$C_5$ alkyl optionally substituted with 1 thru 3 $-Cl$ or $-F$, $-\phi$ optionally substituted with $C_1$-$C_5$ alkyl, $-Cl$, $-OCH_3$, or $-NO_2$.

It is preferred that the weak purification reagent is selected from the group consisting of water, methanol and ethanol; it is more preferred that the weak purification reagent is water. To be operable the acid should produce a pH of less than 4, preferably less than one and even more preferably less than 0. The contacting may be performed either in the absence or presence of an organic solvent. The mixture of 2,4-di(1-pyrrolidinyl)-6-chloropyrimidine (III), 4,6-di(1-pyrrolidinyl)-2-chloropyrimidine (IV), weak purification reagent, and acid are mixed at a temperature such that the undesired 4,6-di(1-pyrrolidinyl)-2-chloropyrimidine (IV) isomer reacts in a convenient period of time. The acid can be either a Lewis acid or a protic acid. A Lewis acid is any compound with a vacant orbital, see "Advanced Organic Chemistry" by J. March, Third Ed. (1985) John Wiley & Sons, p 227. The term compound as used in defining Lewis acids includes parts of a compound such as a cation. It is preferred that the Lewis acid be selected from the group consisting of compounds of the formula $M-L_{n_2}$ where M is selected from the group consisting of boron, aluminum, copper, zinc, silicon, titanium and tin,
L is selected from the group consisting of $-F$, $-Cl$, $-O-CO-CH_3$, $-Br$, $OL_1$ where $L_1$ is $C_1$-$C_4$ alkyl, $n_2$ is 1 thru 6.

It is more preferred that the Lewis acid be selected from the group consisting of boron trifluoride, aluminum trichloride, titanium tetrachloride and tin tetrachloride. It is preferred that the protic acid be an acid with a $pK_a$ of <4. It is more preferred that the protic acid be selected from the group consisting of hydrochloric, hydrobromic, hydroiodic, perchloric, fluoboric, trifluoroacetic, trichloroacetic, phosphoric, sulfuric and acids of the formulas $F_3C-SO_3H$, $Cl-SO_3-H$ and $HO_3SR_6$ where $R_6$ is $C_1$-$C_4$ alkyl or $-\phi$ optionally substituted with $-CH_3$, $-NO_2$, $-Cl$, $-OCH_3$.

The reaction produces a mixture of (III), (IV), (V) and (VI) in which the amount of (IV) is significantly reduced and the ratio of (III)/(IV) is increased, thereby purifying 2,4-di(1-pyrrolidinyl)-6-chloropyrimidine (III). It is preferred that the amount of the undesired 4,6-di(1-pyrrolidinyl)-2-chloropyrimidine (IV) isomer is reduced such that the ratio of (III) to (IV) expressed as (III)/(VI) is greater than 99/1, preferably greater than 99.5/0.5, even more preferred is 99.9/0.1. The desired 2,4-di(1-pyrrolidinyl)-6-chloropyrimidine (III) is then separated from the reaction mixture by physical means as is known to those skilled in the art. A convenient method, if the weak purification reagent is water, is partitioning between water and a water immiscible organic solvent. If the separation means is partitioning, it is preferred that the pH be less than 4 or greater than 7, more preferably less than 3; a pH of about 2 is even more preferred. The phases are separated and the desired 2,4-di(1-pyrrolidinyl)-6-chloropyrimidine (III) is obtained from the organic phase in the usually manner while the pyrimidine by-products (V) and (VI) and the undesired isomer (IV) remain in the aqueous phase. If the weak purification reagent is not water, then a convenient method of separation is to add water and purify as described above.

PROCESS B requires contacting a strong purification reagent with the mixture of 2,4-di(1-pyrrolidinyl)-6-chloropyrimidine (III) and 4,6-di(1-pyrrolidinyl)-2-chloropyrimidine (IV). Strong purification reagents are those compounds which when reacted with a mixture of 2,4-di(1-pyrrolidinyl)-6-chloropyrimidine (III) and 4,6-di(1-pyrrolidinyl)-2-chloropyrimidine (IV) and reduces the amount of 4,6-di(1-pyrrolidinyl)-2-chloropyrimidine (IV) thereby purifying 2,4-di(1-pyrrolidinyl)-6-chloropyrimidine (III). It is preferred that the amount of the undesired 4,6-di(1-pyrrolidinyl)-2-chloropyrimidine (IV) isomer is reduced such that the ratio of (III) to (IV) expressed as (III)/(IV) is greater than 99/1, preferably greater than 99.5/0.5, even more preferred is 99.9/0.1. When the strong purification reagent is contacted with the mixture of 2,4-di(1-pyrrolidinyl)-6-chloropyrimidine (III) and 4,6-di(1-pyrrolidinyl)-2-chloropyrimidine (IV), a mixture of 2,4-di(1-pyrrolidinyl)-6-chloropyrimidine (III), 4,6-di(1-pyrrolidinyl)-2-chloropyrimidine (IV) and the corresponding 6-substituted-2,4-di(1-pyrrolidinyl)pyrimidines (VII) and 2-substituted-4,6-di(1-pyrrolidinyl)pyrimidines (VIII) in which the substituent (R) is derived from the nucleophilic portion of the strong purification reagent is formed. For example, if the strong purification reagent is benzylamine, the reaction mixture would then contain 2,4-di(1-pyrrolidinyl)-6-chloropyrimidine (III), 4,6-di(1-pyrrolidinyl)-2-chloropyrimidine (IV) and 2,4-di(1-pyrrolidinyl)-6-(benzylamino)pyrimidine (VII, R=NH—CH$_2$-$\phi$) and 4,6-di(1-pyrrolidinyl)-2-(benzylamino)pyrimidine (VIII, R=NH—CH$_2$-$\phi$). Likewise, if the strong purification reagent is sodium t-amylate, the reaction mixture would contain 2,4-di(1-pyrrolidinyl)-6-chloropyrimidine (III), 4,6-di(1-pyrrolidinyl)-2-chloropyrimidine (IV), 2,4-di(1-pyrrolidinyl)-6-(t-amyloxy)pyrimidine (VII, R=O-tAmyl) and 4,6-di(1-pyrrolidinyl)-2-(t-amyloxy)pyrimidine (VIII). Similarly when the strong purification reagent is a thiol anion, the corresponding thioethers are obtained. The 2,4-di(1-pyrrolidinyl)-6-chloropyrimidine (III) may be separated from the reaction mixture by-products by known physical means, such as partitioning, extraction, chromatography, distillation, etc.

An alternative of PROCESS B involves adding piperazine directly to the reaction mixture after the contacting of the mixture of 2,4-di(1-pyrrolidinyl)-6-chloropyrimidine (III) and 4,6-di(1-pyrrolidinyl)-2-chloropyrimidine (IV) with the strong purification reagent to produce a mixture of 2,4-di(1-pyrrolidinyl)-6-(1-piperazinyl)pyrimidine (IX), an isomer of (IX), 2,4-di(1-pyrrolidinyl)-6-substituted pyrimidine (VII) and 4,6-di(1-pyrrolidinyl)-2-substituted pyrimidine (VIII). The desired 2,4-di(1-pyrrolidinyl)-6-(1-piperazinyl)pyrimidine (IX) can be easily separated from the remainder of the mixture by extraction with dilute aqueous acid.

All the above information regarding the purification of 2,4-di(1-pyrrolidinyl)-6-chloropyrimidine (III) from a mixture of 2,4-di(1-pyrrolidinyl)-6-chloropyrimidine (III) and 4,6-di(1-pyrrolidinyl)-2-chloropyrimidine (IV) is equally applicable to the purification of 2,4-di(NR$_8$R$_9$)-6-chloropyrimidine (X) from a mixture of 2,4-di(NR$_8$R$_9$)-6-chloropyrimidine (X) and 4,6-di(NR$_8$R$_9$)-2-chloropyrimidine (XI). It is preferred to purify the 2,4-di(NR$_8$R$_9$)-6-chloropyrimidine (X) by PROCESS A.

DEFINITIONS AND CONVENTIONS

The definitions and explanations below are for the terms as used throughout this entire document including both the specification and the claims.

I. DEFINITIONS

All temperatures are in degrees Centigrade. —$\phi$ refers to phenyl (C$_6$H$_5$).
TLC refers to thin-layer chromatography.
HPLC refers to high-pressure liquid chromatography.
DMSO refers to dimethylsulfoxide.

A weak purification reagent is a compound which when reacted with a mixture of 2,4-di(1-pyrrolidinyl)-6-chloropyrimidine (III) and 4,6-di(1-pyrrolidinyl)-2-chloropyrimidine (IV) reduces the amount of 4,6-di(1-pyrrolidinyl)-2-chloropyrimidine (IV) such that the ratio of (III)/(IV) is increased, thereby purifying 2,4-di(1-pyrrolidinyl)-6-chloropyrimidine (III), but only if a sufficient amount of an acid to make the pH less than 4 is present during the contacting of the 2,4-di(1-pyrrolidinyl)-6-chloropyrimidine (III) and 4,6-di(1-pyrrolidinyl)-2-chloropyrimidine (IV) with the weak purification reagent.

A strong purification reagent is a compound which when reacted with a mixture of 2,4-di(1-pyrrolidinyl)-6-chloropyrimidine (III) and 4,6-di(1-pyrrolidinyl)-2-chloropyrimidine (IV) reduces the amount of 4,6-di(1-pyrrolidinyl)-2-chloropyrimidine (IV) such that the ratio of (III)/(IV) is increased, thereby purifying 2,4-di(1-pyrrolidinyl)-6-chloropyrimidine (III).

Isopar H is a high boiling mixture of hydrocarbons.
When solvent pairs are used, the ratios of solvents used are volume/volume (v/v).
When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

Preparation a the mixture of 2,4-di(1-pyrrolidinyl)-6-chloropyrimidine (III) and 4,6-di(1-pyrrolidinyl)-2-chloropyrimidine (IV)

A solution of 2,4,6-trichloropyrimidine (50.0 g) in heptane (500 ml) is added to a flask containing sodium carbonate (58.0 g). Water (80 ml) is added. The mixture is then treated dropwise with pyrrolidine (55.0 ml) at a rate such that the pot temperature remains less than 80°. When the addition is complete, the temperature is adjusted to 80° and stirred until the reaction is complete (12 hr) as measured by TLC. Water (240 ml) is then added, the pot temperature adjusted to 70°, and the layers separated. The aqueous layer is back-extracted with heptane at 70°. The organic extracts are combined and used in EXAMPLE 1. HPLC analysis indicates that the ratio of (III)/(IV) is 97.1/2.9.

PREPARATION 2

Preparation a the mixture of 2,4-di(1-pyrrolidinyl)-6-chloropyrimidine (III) and 4,6-di(1-pyrrolidinyl)-2-chloropyrimidine (IV)

A solution of 2,4,6-trichloropyrimidine (10.0 g) in Isopar H (50 ml) is treated with water (25 ml) followed by pyrrolidine (25.0 ml). During pyrrolidine addition the pot temperature rose to 71°. The reaction mixture is then refluxed for 20 min, at which time conversion to a 93.6/6.4 mixture of 2,4-di-1-pyrrolidinyl-6-chloropyrimidine (III) and 4,6-di-1-pyrrolidinyl-2-chloropyrimidine (IV) is complete by HPLC. The pot temperature is adjusted to 80°±5°, the aqueous layer separated, and the organic layer washed with sodium bicarbonate (5%, 30 ml) followed by water (30 ml). The organic layer was then concentrated under reduced pressure with intermittent addition of heptane to give the title compounds in a ratio of 93.6/6.4.

PREPARATION 3

Preparation a the mixture of 2,4-di(1-pyrrolidinyl)-6-chloropyrimidine (III) and 4,6-di(1-pyrrolidinyl)-2-chloropyrimidine (IV)

A solution of 2,4,6-trichloropyrimide (10.0 g) and 1,4 dibromobenzene (internal standard for HPLC, 1.0 g) in Isopar H (70 ml) is cooled to $-14°$ and treated over 45 min with a solution of pyrrolidine (20.0 ml) in heptane (25 ml). During the addition the pot temperature rose to 0°. The reaction mixture is rinsed in with Isopar H (5 ml). The slurry is stirred at 20°-25° overnight and then warmed to 80°. HPLC analysis indicated that the reaction mixture contained the title compounds in a ratio of 94.2/5.8.

EXAMPLE 1

Purification of the mixture of 2,4-di(1-pyrrolidinyl)-6-chloropyrimidine (III) and 4,6-di(1-pyrrolidinyl)-2-chloropyrimidine (IV) (PROCESS A)

A mixture of 2,4-di(1-pyrrolidinyl)-6-chloropyrimidine (III, PREPARATION 1,97.1 parts) and 4,6-di(1-pyrrolidinyl)-2-chloropyrimidine (IV, PREPARATION 1, 2.9 parts) is cooled to 22° and treated with aqueous hydrochloric acid (32.%, 150 ml). The resulting two-phase mixture is then stirred at 40°-50° for 4-5 hours, at which time the normalized ratio of 2,4-di-(1-pyrrolidinyl)-6-chloropyrimidine (III) to 4,6-di-(1-pyrrolidinyl)-2-chloropyrimidine (IV) to 2,4-di-(1-pyrrolidinyl)-6-pyrimidone (V) to 4,6-di-(1-pyrrolidinyl)-2-pyrimidone (VI is 94.872/.015/2.222/2.891. The reaction mixture is then cooled to 14° and treated with sodium hydroxide (50.%) at a rate such that the pot temperature remains at 50°. The resulting slurry is then heated to 70°, water (75 ml) is added, and the pH adjusted to 1.8 to 2.0 by addition of aqueous sodium hydroxide (50%, 3 ml). During all the subsequent extractions, the pot temperature is kept at >65°. The organic layer is separated and washed with aqueous sodium hydroxide (4%, 54 ml) followed by water (50 ml). Both aqueous extracts are back-extracted with the same heptane (50 ml). The three organic layers are then combined and concentrated to drynes. The residue is treated with Isopar H (90 ml), sodium carbonate (28.8 g), anhydrous piperazine (132.0 g), and octane (30 ml). The resulting slurry is then heated at 133°-135° for 21 hours, at which time the normalized ratio of 2,4-di-(1-pyrrolidinyl-6-chlropyrimidine (III) to 2,6-di-(1-pyrrolidinyl)-4-(1-piperazinyl)pyrimidine to bisadduct is 0.002/97.1/2.897. The reaction mixture is then cooled to 100° and treated with toluene (100 ml), water (250 ml of water) and aqueous sodium hydroxide (50%, 15 ml). The pot temperature is adjusted to 85° and kept at >85° during the subsequent extractions. The aqueous layer is separated, diluted with water (50 ml) and back-extracted with toluene (70 ml). The first organic layer is treated with water (250 ml) and the pH adjusted to 3.8 to 4.0 with concentrated aqueous hydrochloric acid. The two-phase mixture is treated with sufficient toluene (140 ml) to dissolve the solids. The aqueous layer is separated and held:

The organic layer is back-extracted with 50 ml of pH 3.8 to 4.0 water. The two aqueous layers are then combined with the above toluene back-extract and the pH adjusted to 3.8 to 4.0 by the addition of concentrated aqueous hydrochloric acid. The organic layer is then treated with water (50 ml of water), the pH adjusted to pH 3.8 to 4.0 with concentrated aqueous hydrochloric acid, and the aqueous layer separated. The two aqueous layers are then combined, cooled to 50°, and the pH adjusted to >10 by the addition of sodium hydroxide (50%, 30 ml). The resulting slurry is treated with toluene (200 ml) and Isopar H (100 ml). The temperature is adjusted to 80° and kept at >80° during the subsequent extractions. The aqueous phase is separated and the organic phase is washed with water (4×100 ml). Each aqueous extract is back-extracted with a mixture of toluene (75 ml) and Isopar H (25 ml). The two organic layers were combined and the toluene removed under reduced pressure. Isopar H (310 ml) is added intermittently to maintain a stirrable slurry. When all the toluene is removed the mixture is cooled to $-15°$ and filtered. The cake is washed with $-15°$ heptane (300 ml) and dried (80°/~60 mm) to give 2,4-di-(1-pyrrolidinyl)-6-(1-piperazinyl)pyrimidine (IX). The amount of 4,6-di-(1-pyrrolidinyl)-2-(1-piperazinyl)pyrimidine is less than 0.1% by HPLC.

EXAMPLES 2-4

Purification of the mixture of
2,4-di(1-pyrrolidinyl)-6-chloropyrimidine (III) and
4,6-di(1-pyrrolidinyl)-2-chloropyrimidine (IV)
(PROCESS A)

Following the general procedure of EXAMPLE 1 (PROCESS A) and making non-critical variations and using water as the weak purification reagent, and concentrated hydrochloric acid a mixture of 2,4-di(1-pyrrolidinyl)-6-chloropyrimidine (III) and 4,6-di(1-pyrrolidinyl)-2-chloropyrimidine (IV) is purified as set forth below:

| EXAMPLE # | Temperature | Time | (III)/(IV) |
|---|---|---|---|
| 2 | 44° | 3.5 hr | 99.85/0.15 |
| 3 | 36° | 5 hr | 99.96/0.04 |
| 4 | 25° | 17 hr | 99.5/0.5 |

EXAMPLE 5

Purification of the mixture of
2,4-di(1-pyrrolidinyl)-6-chloropyrimidine (III) and
4,6-di(1-pyrrolidinyl)-2-chloropyrimidine (IV)
(PROCESS B) by treatment with sodium amylate and
preparation of
2,6-di-(1-pyrrolidinyl)-4-(1-piperazinyl)pyrimidine (IX)

A mixture of 2,4-di(1-pyrrolidinyl)-6-chloropyrimidine (III) and 4,6-di(1-pyrrolidinyl)-2-chloropyrimidine (IV) in a 93.6/6.4 ratio (PREPARATION 2) is treated with biphenyl (0.5189 g; internal standard for HPLC), toluene (7 ml) and sodium t-amylate (10.48 g), then stirred at 145°±5° C. for 8 hr. The yield of (III) was 89.8% (overall from 2,4,6-trichloropyrimidine, determined by HPLC) and that of (IV) was 0.06%. The reaction mixture was then cooled to 90° and treated with water (30 ml) and pH 7 buffer (40 ml). The pH is adjusted to 2.8 with concentrated hydrochloric acid, the layers separated, and the aqueous layer extracted with toluene (2×20 ml). The organic layers are combined and extracted with concentrated hydrochloric acid (20 ml, then 5 ml). Each aqueous layer is back extracted in sequence with a 15 ml portions of toluene/heptane (2/1). The aqueous layers are combined, diluted with water (50 ml), covered with toluene (30 ml), and the pH adjusted to 11.4 by the addition of aqueous sodium hydroxide (50%, 14 ml). The layers are separated and the aqueous layer is extracted with toluene (2×30 ml) followed by methylene chloride (3×20 ml). The organic layers are washed with water, combined, and concentrated to give the title compounds in a ratio of 99.98/0.02.

The concentrate is treated with piperazine (33.59 g), sodium phosphate (7.9 g) and toluene (34 ml), then heated to 145°±5° for approximately 3 hr., at which time normalized ratio of 2,4-di(1-pyrrolidinyl)-6-chloropyrimidine (III) to 2,6-di-(1-pyrrolidinyl)-4-(1-piperazinyl)pyrimidine (IX) to the bisadduct was 0.8/97.5/1.7 by HPLC. The reaction mixture is then treated with toluene (16 ml), water (75 ml) and sodium hydroxide (50%, 7.2 ml). The pot temperature is adjusted to 90° and the two lower (aqueous) layers are separated from the upper (organic) layer. The two lower aqueous layers are diluted with water (50 ml) and toluene (30 ml) is added. Two homogeneous phases resulted. The layers are separated and the aqueous layer extracted with toluene (25 ml). The aqueous layer is then diluted with water (300 ml), cooled to 20°-25°, and extracted with methylene chloride. All the organic layers are combined, water (60 ml) is added, the pot temperature adjusted to 60°, and the pH is adjusted to 4.1 by the addition of concentrated hydrochloric acid. The phases are separated and the organic layer extracted with pH 4.2 water (15 ml). Both aqueous layers are extracted in sequence at with toluene (15 ml). The two aqueous layers are combined and the pH adjusted to 12.9 by the addition of sodium hydroxide (50%, 7.5 ml). The resulting slurry is filtered. The cake is washed with water and and dried to give 2,6-di-(1-pyrrolidinyl)-4-(1-piperazinyl)pyrimidine (IX) in pure form. None of the 2-(1-piperazinyl) isomer was detected.

EXAMPLE 6

Purification of the mixture of
2,4-di(1-pyrrolidinyl)-6-chloropyrimidine (III) and
4,6-di(1-pyrrolidinyl)-2-chloropyrimidine (IV)
(PROCESS B) by treatment with pyrrolidine and
preparation of
2,6-di-(1-pyrrolidinyl)-4-(1-piperazinyl)pyrimidine (IX)

A mixture of 2,4-di(1-pyrrolidinyl)-6-chloropyrimidine (III) and 4,6-di(1-pyrrolidinyl)-2-chloropyrimidine (IV) in a 94.2/5.8 ratio (PREPARATION 3) is treated with pyrrolidine (5.0 ml) then heated over 3.5 hr. to 138° and stirred at this temperature for 3.25 hours at which time the ratio of (III)/(IV) is 99.82/0.18. The reaction mixture is treated with water (65 ml), the pot temperature adjusted to 90°, and the aqueous layer separated. The organic layer is then washed with aqueous sodium bicarbonate (5%, 40 ml) followed by water (40 ml). The organic layer which contains (III) is treated with pyridine (100 ml) and piperazine (24.1 g). The resulting slurry is stirred at 155°±5° for 16 hr., at which time the normalized ratio of 2,4-di-(1-pyrrolidinyl)-6-chloropyrimidine (III) to 2,6-di-(1-pyrrolidinyl)-4-(1-piperazinyl)pyrimidine (IX) to bisadduct was 2.1/95.4/2.5. A portion of the reaction mixture (252 ml) is worked up as follows. The mixture is concentrated under reduced pressure to a slurry which is treated with water (60 ml) and heptane. The pH is adjusted to 1.8 by the addition of aqueous sulfuric acid (10%, 85 ml). The aqueous layer is separated, mixed with methylene chloride (40 ml), and the pH adjusted to 3.5 by the addition of sodium hydroxide (15%, 7 ml). The aqueous layer is separated, then washed with methylene chloride (4×30 ml). The pH of the aqueous layer is adjusted to between 3.5 and 3.6 during each extraction. The aqueous layer is mixed with methylene chloride (50 ml) and the pH adjusted to 12.0 by the addition of sodium hydroxide (15%). The organic layer is separated and the aqueous layer is extracted with methylene chloride (30 ml). The two organic layers are combined and concentrated to a solid residue, which was dissolved in aqueous sulfuric acid (10%, 35 ml). The resulting solution is diluted with water (10 ml) and enough aqueous sodium hydroxide (15%) to adjust pH to 12. The resulting slurry is filtered. The cake is washed with water and dried to give 2,6-di-(1-pyrrolidinyl)-4-(1-piperazinyl)pyrimidine (IX) in pure form. None of the 2-(1-piperazinyl)isomer is detected.

EXAMPLES 7-11

Purification of the mixture of 2,4-di(1-pyrrolidinyl)-6-chloropyrimidine (III) and 4,6-di(1-pyrrolidinyl)-2-chloropyrimidine (IV) (PROCESS A)

Following the general procedure of EXAMPLES 5 and 6 (PROCESS B) and making noncritical variations and using the reaction conditions set forth below (without the addition of piperazine) the mixtures of 2,4-di(1-pyrrolidinyl)-6-chloropyrimidine (III)/4,6-di(1-pyrrolidinyl)-2-chloropyrimidine (IV) has the ratios set forth below:

| EXAMPLE # | Purification Reagent | Solvent | Temp | Time | (III)/(IV) |
|---|---|---|---|---|---|
| 7 | benzylamine | Isopar H | 190° | 18 hr | >99.9/0.1 |
| 8 | piperazine | pyridine | 130° | 16.5 hr | >99.9/0.1 |
| 9 | 1,1-dimethylhydrazine | toluene | 135° | 2.5 hr | 99.9/0.1 |
| 10 | potassium t-butoxide | DMSO | 52° | 6 hr | 99.2/0.8 |
| 11 | sodium methoxide | methanol | 85° | 16 hr | 99.7/0.3 |

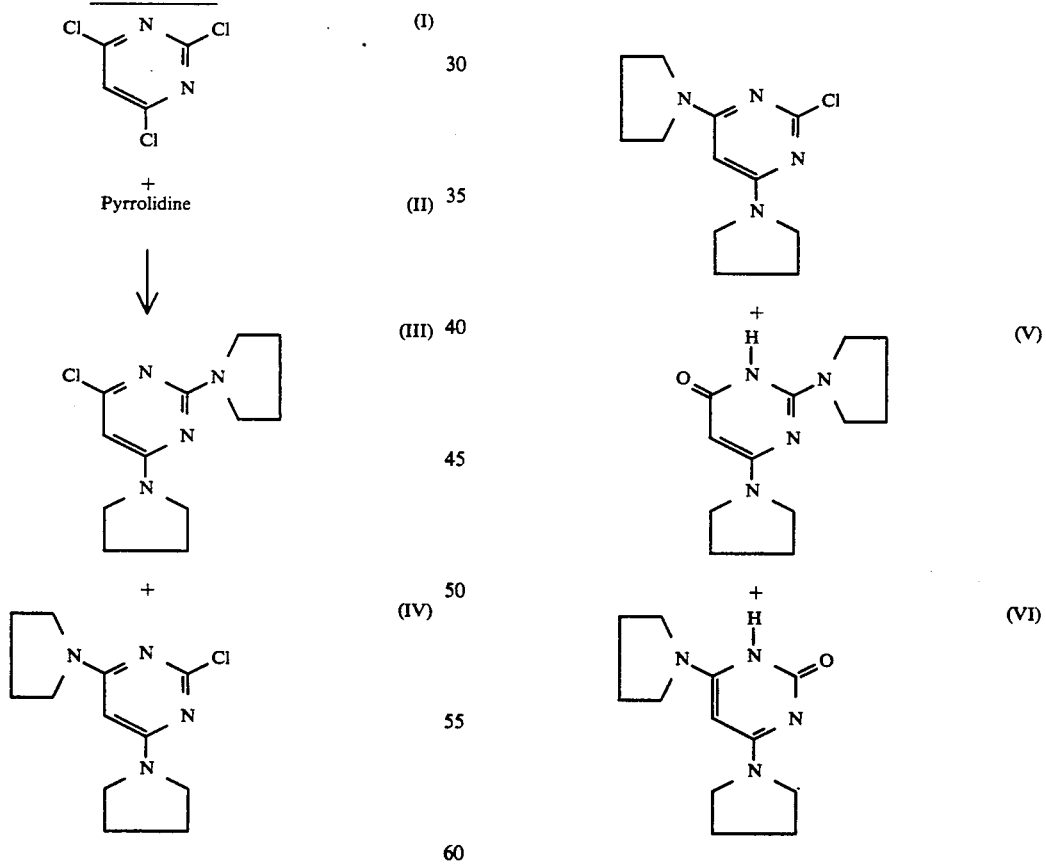

-continued
CHART C

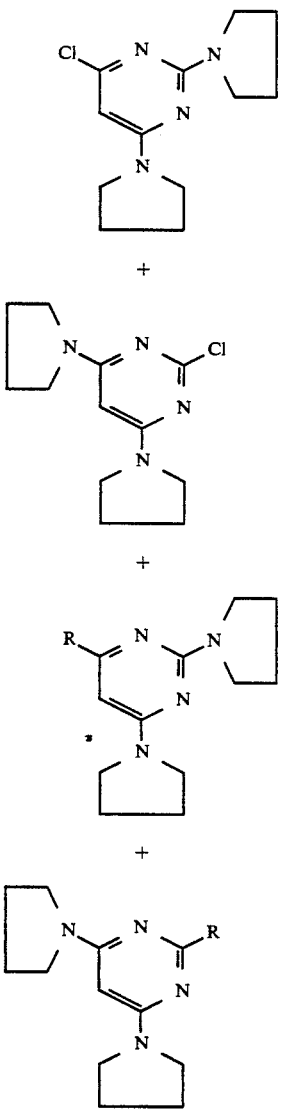

CHART D

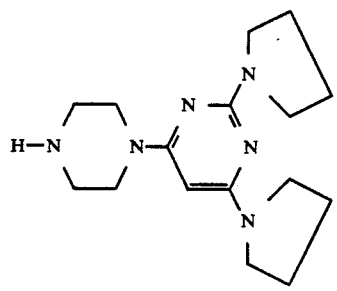

We claim:
1. A process for purification of 2,4-di(1-pyrrolidinyl)-6-chloropyrimidine (III)

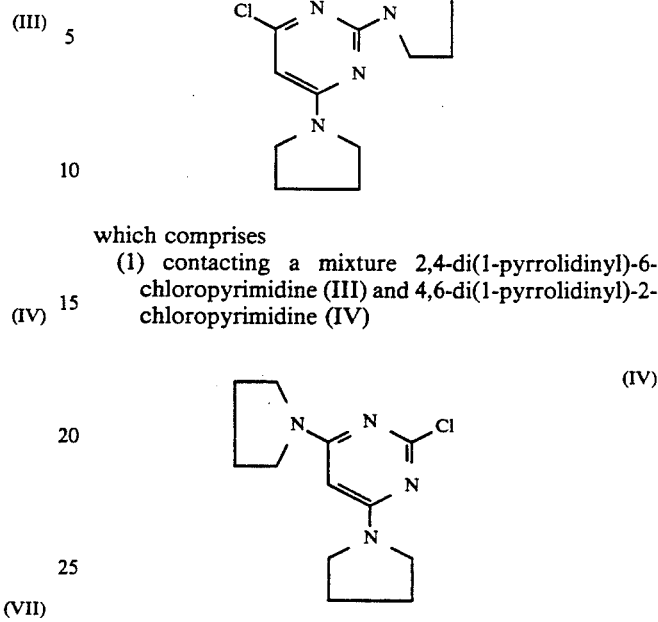

which comprises
(1) contacting a mixture 2,4-di(1-pyrrolidinyl)-6-chloropyrimidine (III) and 4,6-di(1-pyrrolidinyl)-2-chloropyrimidine (IV)

with a weak purification reagent in the presence of a sufficient amount of an acid to make the pH less than 4 and
(2) separating the 2,4-di(1-pyrrolidinyl)-6-chloropyrimidine (III) by physical means from the pyrimidine byproducts (V) and (VI).

2. A process for purification of 2,4-di(1-pyrrolidinyl)-6-chloropyrimidine (III) according to claim 1 where the weak purification reagent is selected from the group consisting of water, glycerol, ethylene glycol, propylene glycol and alcohols of the formula $R_a(-O-CH_2-CH_2)_{n1}-OH$ where $n_1$ is 0 thru 20, $R_a$ is
$C_1-C_5$ alkyl optionally substituted with 1 thru 3 —Cl or —F,
—φ optionally substituted with $C_1-C_5$ alkyl, —Cl, —OCH$_3$, or —NO$_2$.

3. A process for purification of 2,4-di(1-pyrrolidinyl)-6-chloropyrimidine (III) according to claim 1 where the weak purification reagent is selected from the group consisting of water, methanol and ethanol.

4. A process for purification of 2,4-di(1-pyrrolidinyl)-6-chloropyrimidine (III) according to claim 1 where the weak purification reagent is water.

5. A process for purification of 2,4-di(1-pyrrolidinyl)-6-chloropyrimidine (III) according to claim 1 where the acid is a Lewis acid or a protic acid.

6. A process for purification of 2,4-di(1-pyrrolidinyl)-6-chloropyrimidine (III) according to claim 1 where the Lewis acid is selected from the group consisting of compounds of the formula $M-L_{n2}$ where
M is selected from the group consisting of boron, aluminum, copper, zinc, silicon, titanium and tin,
L is selected from the group consisting of —F, —Cl, —O—CO—CH$_3$, —Br, OL$_1$ where L$_1$ is $C_1-C_4$ alkyl,
$n_2$ is 1 thru 6.

7. A process for purification of 2,4-di(1-pyrrolidinyl)-6-chloropyrimidine (III) according to claim 6 where the Lewis acid is selected from the group consisting of boron trifluoride, aluminum trichloride, titanium tetrachloride and tin tetrachloride.

8. A process for purification of 2,4-di(1-pyrrolidinyl)-6-chloropyrimidine (III) according to claim 5 where the protic acid is an acid with a $pK_a$ of $<4$.

9. A process for purification of 2,4-di(1-pyrrolidinyl)-6-chloropyrimidine (III) according to claim 8 where the protic acid is selected from the group consisting of hydrochloric, hydrobromic, hydroiodic, perchloric, fluoboric, trifluoroacetic, trichloroacetic, phosphoric, sulfuric and acids of the formulas $F_3C-SO_3H$, $Cl-SO_3-H$ and $HO_3SR_6$ where $R_6$ is $C_1-C_4$ alkyl or $-\phi$ optionally substituted with $-CH_3$, $-NO_2$, $-Cl$, $-OCH_3$.

10. A process for purification of 2,4-di(1-pyrrolidinyl)-6-chloropyrimidine (III) according to claim 1 where the 2,4-di(1-pyrrolidinyl)-6-chloropyrimidine (III) is obtained from the pyrimidine by-products (V) and (VI) by partitioning between water and a water immiscible organic solvent.

11. A process for purification of 2,4-di(1-pyrrolidinyl)-6-chloropyrimidine (III) according to claim 1 where the 2,4-di(1-pyrrolidinyl)-6-chloropyrimidine (III)/4,6-di(1-pyrrolidinyl)-2-chloropyrimidine (IV) ratio is greater than 99/1.

12. A process for purification of 2,4-di(1-pyrrolidinyl)-6-chloropyrimidine (III) according to claim 1 where the 2,4-di(1-pyrrolidinyl)-6-chloropyrimidine (III)/4,6-di(1-pyrrolidinyl)-2-chloropyrimidine (IV) ratio is greater than 99.5/0.5.

13. A process for purification of 2,4-di(1-pyrrolidinyl)-6-chloropyrimidine (III) according to claim 1 where the 2,4-di(1-pyrrolidinyl)-6-chloropyrimidine (III)/4,6-di(1-pyrrolidinyl)-2-chloropyrimidine (IV) ratio is greater than 99.9/0.1.

14. A process for the purification of 2,4-di(1-pyrrolidinyl)-6-chloropyrimidine (III)

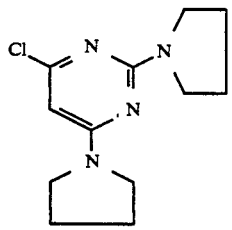

(III)

which comprises
(1) contacting a mixture 2,4-di(1-pyrrolidinyl)-6-chloropyrimidine (III) and 4,6-di(1-pyrrolidinyl)-2-chloropyrimidine (IV)

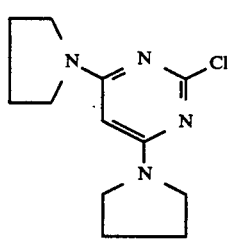

(IV)

with a strong purification reagent and
(2) separating the 2,4-di(1-pyrrolidinyl)-6-chloropyrimidine (III) by physical means.

15. A process for purification of 2,4-di(1-pyrrolidinyl)-6-chloropyrimidine (III) according to claim 14 where the strong purification reagent is selected from the group consisting of $NR_1R_2R_3$ where $R_1$, $R_2$ and $R_3$ are the same or different and are selected from the group consisting of
—H,
$C_1-C_6$ alkyl,
—$\phi$ optionally substituted with 1 thru 3 —Cl, —CH$_3$
and where two of $R_1$, $R_2$ and $R_3$ can be taken together with the attached nitrogen atom to form a heterocyclic ring selected from the group consisting of pyrrolidine, piperazine, pyridine, pyrimidine and morpholine,
$OR_4^-$ where $R_4$ is $C_1-C_6$ alkyl,
$SR_4^-$ where $R_4$ is as defined above,
1,1-dimethylhydrazine,
$R_1R_2N-NR_1R_2$ where $R_1$ and $R_2$ are as defined above,
$H_2N-NH-CO-NH_2$,
$H_2N-NH-CO_2-R_1$ where $R_1$ as is defined above,
$H_2N-NH-SO_2-R_5$ where $R_5$ is $C_1-C_6$ alkyl or $-\phi$ optionally substituted with 1 thru 3 —Cl or —CH$_3$,
$R_1R_2N-OR_3$ where $R_1$, $R_2$ and $R_3$ are as defined above,
$R_1OO^-$ where $R_1$ is as defined above,
$R_1-CO_3^-$ where $R_1$ is as defined above,
$CO_2^{-2}$,
$PO_4^{-3}$,
$R_7-Mg-X_1$ where $R_7$ is $C_1-C_8$ alkyl or $-\phi$ and where $X_1$ is —Cl, —Br, —I,
$R_7-Mg-R_7$ where $R_7$ is as defined above,
$R_7-Li$ where $R_7$ is as defined above,
diisobutylaluminum hydride (DIBAL),
sodium borohydride (NaBH$_4$) and
lithium aluminum hydride (LiAlH$_4$).

16. A process for purification of 2,4-di(1-pyrrolidinyl)-6-chloropyrimidine (III) according to claim 15 where the strong purification reagent is selected from the group consisting of benzylamine, 1,1-dimethylhydrazine, piperazine, pyrrolidine, methoxide, ethoxide, t-butoxide, t-amylate and isopropoxide.

17. A process for purification of 2,4-di(NR$_8$R$_9$)-6-chloropyrimidine (X) where $R_8$ and $R_9$ are the same or different and are
—H,
$C_1-C_6$ alkyl,
—CH$_2$—CH=CH$_2$,
—CH$_2$—CH$_2$—CH$_2$—OCH$_3$,
—$\phi$ optionally substituted with 1 thru 3 —Cl, —CH$_3$
and where two of $R_8$ and $R_9$ can be taken together with the attached nitrogen atom to form a heterocyclic ring selected from the group consisting of pyrrolidinyl, piperazinyl, pyridinyl, pyrimidinyl and morpholinyl, which comprises
(1) contacting a mixture 2,4-di(NR$_8$R$_9$)-6-chloropyrimidine (X) and 4,6-di(NR$_8$R$_9$)-2-chloropyrimidine (XI) where $R_{8=}$ and $R_9$ are as defined above, with a weak purification reagent in the presence of a sufficient amount of an acid to make the pH less than 4 and
(2) separating the 2,4-di(NR$_8$R$_9$)-6-chloropyrimidine (III) by physical means.

18. A process for purification of 2,4-di(NR$_8$R$_9$)-6-chloropyrimidine (X) according to claim 17 where the weak purification reagent is selected from the group consisting of water, glycerol, ethylene glycol, propylene glycol and alcohols of the formula $R_a(-O-CH_2-CH_2)_{n1}-OH$ where $n_1$ is 0 thru 20, $R_a$ is
$C_1-C_5$ alkyl optionally substituted with 1 thru 3 —Cl or —F, —φ optionally substituted with $C_1$-$C_5$ alkyl, —Cl, —OCH$_3$, or —NO$_2$.

19. A process for purification of 2,4-di(NR$_8$R$_9$)-6-chloropyrimidine (X) according to claim 17 where the acid is a Lewis acid or a protic acid.

20. A process for purification of 2,4-di(NR$_8$R$_9$)-6-chloropyrimidine (X) according to claim 17 where the Lewis acid is selected from the group consisting of compounds of the formula M-L$_{n2}$ where M is selected from the group consisting of boron, aluminum, copper, zinc, silicon, titanium and tin, L is selected from the group consisting of —F, —Cl, —O—CO—CH$_3$, —Br, OL$_1$ where L$_1$ is $C_1$-$C_4$ alkyl, n$_2$ is 1 thru 6.

21. A process for purification of 2,4-di(1-pyrrolidinyl)-6-chloropyrimidine (III) according to claim 19 where the protic acid is an acid with a pK$_a$ of <4.

22. A process for purification of 2,4-di(NR$_8$R$_9$)-6-chloropyrimidine (X) according to claim 17 where the 2,4-di(NR$_8$R$_9$)-6-chloropyrimidine (X) is obtained from the pyrimidine by-products by partitioning between water and a water immiscible organic solvent.

23. A process for purification of 2,4-di(NR$_8$R$_9$)-6-chloropyrimidine (X) according to claim 17 where the 2,4-di(NR$_8$R$_9$)-6-chloropyrimidine (X)/4,6-di(NR$_8$R$_9$)-2-chloropyrimidine (XI) ratio is greater than 99/1.

24. A process for purification of 2,4-di(NR$_8$R$_9$)-6-chloropyrimidine (X) according to claim 17 where the 2,4-di(NR$_8$R$_9$)-6-chloropyrimidine (X) is 2,4-di(isopropylamine)-6-chloropyrimidine.

25. A process for the preparation of 2,4-di(1-pyrrolidinyl)-6-(1-piperazinyl)pyrimidine (IX)

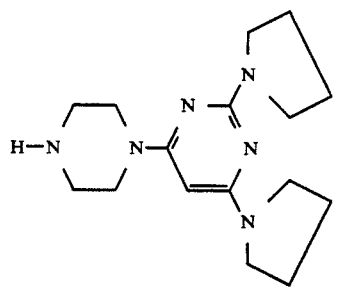

(IX)

which comprises (1) contacting a mixture 2,4-di(1-pyrrolidinyl)-6-chloropyrimidine (III)

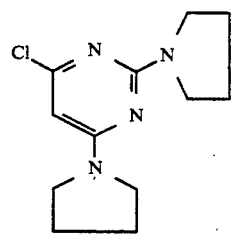

(III)

and 4,6-di(1-pyrrolidinyl)-2-chloropyrimidine (IV)

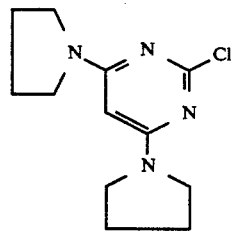

(IV)

with a weak purification reagent in the presence of a sufficient amount of an acid to make the pH less than 4 and (2) contacting the reaction mixture of step (1) with piperazine.

26. A process for the preparation of 2,4-di(1-pyrrolidinyl)-6-(1-piperazinyl)pyrimidine (IX) according to claim 25 where the weak purification reagent is selected from the group consisting of water, glycerol, ethylene glycol, propylene glycol and alcohols of the formula R$_a$(—O—CH$_2$—CH$_2$)$_{n1}$—OH where n$_1$ is 0 thru 20, R$_a$ is $C_1$-$C_5$ alkyl optionally substituted with 1 thru 3—Cl or —F, —φ optionally substituted with $C_1$-$C_5$ alkyl, —Cl, —OCH$_3$, or —NO$_2$.

27. A process for the preparation of 2,4-di(1-pyrrolidinyl)-6-(1-piperazinyl)pyrimidine (IX) according to claim 25 where the acid is a Lewis acid or a protic acid.

28. A process for the preparation of 2,4-di(1-pyrrolidinyl)-6-(1-piperazinyl)pyrimidine (IX) according to claim 25 where the Lewis acid is selected from the group consisting of compounds of the formula M-L$_{n2}$ where M is selected from the group consisting of boron, aluminum, copper, zinc, silicon, titanium and tin, L is selected from the group consisting of —F, —Cl, —O—CO—CH$_3$, —Br, OL$_1$ where L$_1$ is $C_1$-$C_4$ alkyl, n$_2$ is 1 thru 6.

29. A process for the preparation of 2,4-di(1-pyrrolidinyl)-6-(1-piperazinyl)pyrimidine (IX) according to claim 27 where the protic acid is an acid with a pK$_a$ of <4.

* * * * *